United States Patent
Hall et al.

(10) Patent No.: US 10,280,417 B2
(45) Date of Patent: May 7, 2019

(54) COMPOSITIONS, METHODS AND APPARATUS FOR OLIGONUCLEOTIDES SYNTHESIS

(71) Applicant: Gen9, Inc., Cambridge, MA (US)

(72) Inventors: Giles F. Hall, Somerville, MA (US); Scott S. Lawton, Bedford, MA (US)

(73) Assignee: Gen 9, Inc., Cambridge, MA (US)

( * ) Notice: Subject to any disclaimer, the term of this patent is extended or adjusted under 35 U.S.C. 154(b) by 600 days.

(21) Appl. No.: 14/765,961

(22) PCT Filed: Mar. 13, 2014

(86) PCT No.: PCT/US2014/025610
§ 371 (c)(1),
(2) Date: Aug. 5, 2015

(87) PCT Pub. No.: WO2014/160004
PCT Pub. Date: Oct. 2, 2014

(65) Prior Publication Data
US 2016/0122755 A1  May 5, 2016

Related U.S. Application Data

(60) Provisional application No. 61/778,973, filed on Mar. 13, 2013.

(51) Int. Cl.
| | | |
|---|---|---|
| *C12N 15/10* | (2006.01) | |
| *C12P 19/34* | (2006.01) | |
| *C40B 40/06* | (2006.01) | |
| *C12N 15/66* | (2006.01) | |

(52) U.S. Cl.
CPC ......... *C12N 15/1068* (2013.01); *C12N 15/10* (2013.01); *C12N 15/1031* (2013.01); *C12N 15/66* (2013.01); *C12P 19/34* (2013.01); *C40B 40/06* (2013.01)

(58) Field of Classification Search
None
See application file for complete search history.

(56) References Cited

U.S. PATENT DOCUMENTS

| | | |
|---|---|---|
| 4,500,707 A | 2/1985 | Caruthers et al. |
| 4,725,677 A | 2/1988 | Koster et al. |
| 5,047,524 A | 9/1991 | Andrus et al. |
| 8,808,986 B2 | 8/2014 | Jacobson et al. |
| 2002/0076716 A1 | 6/2002 | Sabanayagam et al. |
| 2011/0039304 A1 | 2/2011 | Church et al. |
| 2011/0217738 A1 | 9/2011 | Jacobson |
| 2013/0059296 A1 | 3/2013 | Jacobson et al. |
| 2014/0045728 A1 | 2/2014 | Church et al. |
| 2014/0141982 A1 | 5/2014 | Jacobson et al. |
| 2015/0368687 A1 | 12/2015 | Saaem et al. |

FOREIGN PATENT DOCUMENTS

| | | |
|---|---|---|
| WO | WO-2007123742 A2 | 11/2007 |
| WO | WO-2010/025310 A2 | 3/2010 |
| WO | WO-2011085075 A2 | 7/2011 |
| WO | 2013032850 | 3/2013 |
| WO | WO-2013/163263 A2 | 10/2013 |
| WO | WO-2014160004 A1 | 10/2014 |
| WO | WO-2014160059 A1 | 10/2014 |

OTHER PUBLICATIONS

International Preliminary Report on Patentability issued in International Patent Application PCT/US2014/025610 dated Sep. 24, 2015.
Richmond, K. et al., "Amplification and Assembly of Chip-Eluted DNA (AACED): A Method for High-Throughput Gene Synthesis.", Nucleic Acids Research, vol. 32, No. 17, pp. 5011-5018, Sep. 24, 2004.
International Search Report for International Application No. PCT/2014/025610 dated Jul. 7, 2014.
Biswas, I. and Hsieh, P., Identification and Characterization of a Thermostable MutS Homolog from Thermus aquaticus, Journal of Biological Chemistry, 271(9): 5040-5048 (1996).
Written Opinion for PCT/US2014/025610, 8 pages, ISA/US (dated Jul. 7, 2014).

*Primary Examiner* — Kaijiang Zhang
(74) *Attorney, Agent, or Firm* — Choate, Hall & Stewart LLP; Brenda Herschbach Jarrell; Robert N. Sahr (57) ABSTRACT

Aspects of the invention relate to methods, compositions for synthesizing oligonucleotides having a predefined sequence.

21 Claims, 1 Drawing Sheet

Direction of oligonucleotide synthesis

COMPOSITIONS, METHODS AND APPARATUS FOR OLIGONUCLEOTIDES SYNTHESIS

RELATED APPLICATIONS

This application is a National Phase application of International Application No. PCT/US2014/025610, filed Mar. 13, 2014 which claims the benefit of and priority to U.S. Provisional Application No. 61/778,973, filed Mar. 13, 2013, the contents of each foregoing applications are incorporated herein by reference in their entirety.

FIELD OF THE INVENTION

Methods and compositions of the invention relate to oligonucleotide synthesis, and particularly to the synthesis of high fidelity oligonucleotides on an array.

BACKGROUND

Recombinant and synthetic nucleic acids have many applications in research, industry, agriculture, and medicine. Recombinant and synthetic nucleic acids can be used to express and obtain large amounts of polypeptides, including enzymes, antibodies, growth factors, receptors, and other polypeptides that may be used for a variety of medical, industrial, or agricultural purposes. Recombinant and synthetic nucleic acids also can be used to produce genetically modified organisms including modified bacteria, yeast, mammals, plants, and other organisms. Genetically modified organisms may be used in research (e.g., as animal models of disease, as tools for understanding biological processes, etc.), in industry (e.g., as host organisms for protein expression, as bioreactors for generating industrial products, as tools for environmental remediation, for isolating or modifying natural compounds with industrial applications, etc.), in agriculture (e.g., modified crops with increased yield or increased resistance to disease or environmental stress, etc.), and for other applications. Recombinant and synthetic nucleic acids also may be used as therapeutic compositions (e.g., for modifying gene expression, for gene therapy, etc.) or as diagnostic tools (e.g., as probes for disease conditions, etc.).

Numerous techniques have been developed for modifying existing nucleic acids (e.g., naturally occurring nucleic acids) to generate recombinant nucleic acids. For example, combinations of nucleic acid amplification, mutagenesis, nuclease digestion, ligation, cloning and other techniques may be used to produce many different recombinant nucleic acids.

Chemically synthesized oligonucleotides are often used as primers or adaptors for nucleic acid amplification, mutagenesis, and cloning. In addition, techniques also are being developed for de novo nucleic acid assembly whereby oligonucleotides are made (e.g., chemically synthesized) and assembled to produce longer target nucleic acids of interest. However, one limitation of currently available assembly techniques is the relatively high error rate during oligonucleotide synthesis. As such, high fidelity, low cost oligonucleotide synthesis methods and apparatus are needed.

SUMMARY OF THE INVENTION

Aspects of the invention generally relate to methods, systems and compositions for preparing and/or assembling high fidelity polymers. It is an object of this invention to provide practical, economical methods of synthesizing custom polynucleotides. It is a further object of the invention to provide methods of producing synthetic polynucleotides that have lower error rates than synthetic polynucleotides made by methods known in the art.

In some embodiments, a method of generating an oligonucleotide having a predefined sequence is provided. In some embodiments, the method comprises (a) designing at least one plurality of oligonucleotides, each oligonucleotide of each plurality of oligonucleotides having a different length, each oligonucleotide having an identical predefined internal sequence and an additional padding nucleotide sequence at the 5' end, wherein each padding nucleotide sequence has a different length, (b) synthesizing the at least one plurality of oligonucleotides on a solid support and (c) isolating the oligonucleotide having the correct predefined internal sequence.

In some embodiments, in the step of designing, the plurality of oligonucleotides have 5' and 3' flanking sequences flanking the 5' and the 3' end of the internal sequence, each of the flanking region comprising a primer recognition site for a primer pair and a restriction enzyme recognition site. The restriction endonuclease can be a type IIS restriction endonuclease.

In some embodiments, the method further comprises amplifying the plurality of oligonucleotides. In some embodiments, the method further comprises exposing the amplified oligonucleotides to a restriction enzyme under conditions suitable to promote digestion.

In some embodiments, the method further comprises subjecting the plurality of amplified oligonucleotides to error removal prior or after the exposing step. For example, the plurality of amplified oligonucleotides can be contacted with a mismatch binding agent, wherein the mismatch binding agent selectively binds and cleaves the double-stranded oligonucleotides comprising a mismatch.

In some embodiments, in the step of designing, the padding nucleotide sequence is between the primer recognition site and the restriction enzyme recognition site. In other embodiments, in the step of designing, the padding nucleotide sequence is upstream the primer recognition site and upstream the restriction enzyme recognition site. In some embodiments, the padding nucleotide sequence is from 4 nucleotides long to 10 nucleotides long.

In some embodiments, in the step of synthesizing, the plurality of oligonucleotides comprises error-containing oligonucleotides and error-free oligonucleotides.

In some embodiments, the step of isolating comprises sequencing the oligonucleotides.

Aspects of the invention relate to redundant arrays. In some embodiments, the redundant array comprises at least one plurality oligonucleotide sequences, each oligonucleotide of each plurality of oligonucleotides having a different length, each oligonucleotide having an identical predefined internal sequence and an additional padding nucleotide sequence at the 5' end, the redundant array comprising redundant internal sequences. Each padding nucleotide sequence can have a different length. The plurality of oligonucleotides can have 5' and 3' flanking sequences flanking the 5' end and the 3' end of the internal sequence. In some embodiments, the 5' flanking region can comprise from 5' to 3' a primer recognition site (also referred herein as primer binding sequence) for a primer pair and a restriction enzyme recognition site, the padding nucleotide sequence being between the primer recognition site and the restriction enzyme recognition site, and the 3' flanking region can comprise, from 5' to 3', a restriction enzyme recognition site and primer recognition site. In other embodiments, the 5' flanking region can comprise, from 5' to 3', a primer recognition site for a primer pair and a restriction enzyme recognition site, wherein the padding nucleotide sequence is 5' of the primer recognition site, and the 3' flanking region can comprise from 5' to 3' a restriction enzyme recognition site and primer recognition site.

In some embodiments, each internal sequence on the redundant array can be represented by two sets of oligonucleotides, the first set of oligonucleotides being a reverse-complement of the first set of oligonucleotides.

Aspects of the invention relate to compositions for the assembly of a target nucleic acid having a predefined sequence. In some embodiments, the composition comprises a first plurality of oligonucleotides comprising an internal sequence identical to the 5' end of the target nucleic acid, a second plurality of oligonucleotides comprising an internal sequence identical to the 3' end of the target nucleic acid; and optionally one or more plurality of oligonucleotides comprising an internal sequence identical to a different portion of a sequence of a target nucleic acid. The different portions can be an internal sequence of a target nucleic acid. Each of the plurality oligonucleotides can have an overlapping sequence region corresponding to a sequence region in a next oligonucleotide so as to together comprise the target nucleic acid. Each plurality of oligonucleotides can be designed to have an additional padding nucleotide sequence at the 5' end. In some embodiments, each plurality of oligonucleotides can be designed to have 5' and 3' flanking sequences flanking the 5' end and the 3' end of the internal sequence, each of the flanking regions comprising a primer recognition site for a primer pair and a restriction enzyme recognition site.

DETAILED DESCRIPTION OF THE INVENTION

Aspects of the technology provided herein are useful for increasing the accuracy, yield, throughput, and/or cost efficiency of nucleic acid synthesis and assembly reactions. In some aspect, the invention is directed to nucleic acids, polynucleotides or oligonucleotides synthesis having a predetermined sequence on solid supports.

For the purposes of this invention, the terms "oligonucleotide", "polynucleotide" and "nucleic acid" are used interchangeably, unless otherwise noted and refer to at least two nucleotides, ribonucleotides and/or deoxyribonucleotides or a modified form of either type of nucleotides, covalently linked together. The oligonucleotides and nucleic acid molecules of the present invention may be formed from naturally occurring nucleotides, for example forming deoxyribonucleic acid (DNA) or ribonucleic acid (RNA) molecules. Alternatively, the naturally occurring oligonucleotides may include structural modifications to alter their properties, such as in peptide nucleic acids (PNA) or in locked nucleic acids (LNA). The terms should be understood to include equivalents, analogs of either RNA or DNA made from nucleotide analogs and as applicable to the embodiment being described, single-stranded or double-stranded polynucleotides. A "nucleotide" refers to a sub-unit of a nucleic acid and has a phosphate group, a 5 carbon sugar and a nitrogen containing base, as well as functional analogs (whether synthetic or naturally occurring) of such sub-units which in the polymer form (as a polynucleotide) can hybridize with naturally or non-naturally occurring polynucleotides in a sequence specific manner analogous to that of two naturally occurring polynucleotides. Nucleotide sub-units of deoxyribonucleic acids are deoxyribonucleotides, and nucleotide sub-units of ribonucleic acids are ribonucleotides. The term "nucleotide" refers to a nucleoside having a phosphate group on its 3' or 5' sugar hydroxyl group. These nucleotide units may be nucleic acid bases such as guanine, adenine, cytosine, thymine or uracil. The sugar group can be a deoxyribose or ribose. Nucleic acids refer to both naturally occurring and synthetic species formed from naturally occurring subunits. Nucleotides useful in the invention include, for example, naturally-occurring nucleotides (for example, ribonucleotides or deoxyribonucleotides), or natural or synthetic modifications of nucleotides, or artificial bases. An oligonucleotide synthesized according to the invention, generally contains plosophodiester bonds, although it may contain alternate backbones comprising for example, phosphoramide, phosphorothioate, phosphorodithioate, O-methylphosphoroamidite linkages, non-ionic backbones, non-ribose backbones, peptide nucleic acid backbones and linkages. Nucleic acids include peptide nucleic acids and locked nucleic acids.

As used herein, the terms "predetermined sequence" and "predefined sequence" are used interchangeably and means that the sequence of the nucleic acid is known and chosen before synthesis or assembly of the nucleic acid. In particular, aspects of the invention are described herein primarily with regard to the preparation of nucleic acid molecules, the sequence of the nucleic acids being known and chosen before the synthesis or assembly of the nucleic acid molecules. In some embodiments of the technology provided herein, immobilized oligonucleotides or polynucleotides are used as a source of material. In various embodiments, the methods described herein use oligonucleotides, their sequence being determined based on the sequence of the final polynucleotide constructs to be synthesized. In one embodiment, oligonucleotides are short nucleic acid molecules. For example, oligonucleotides may be from 10 to about 300 nucleotides, from 20 to about 400 nucleotides, from 30 to about 500 nucleotides, from 40 to about 600 nucleotides, or more than about 600 nucleotides long. However, shorter or longer oligonucleotides may be used. Oligonucleotides may be designed to have different length.

As used herein the terms "support", "substrate" and "surface" are used interchangeably and refer to a porous or non-porous solvent insoluble material on which polymers such as nucleic acids are synthesized or immobilized. As used herein "porous" means that the material contains pores having substantially uniform diameters (for example in the nm range). A solid support refers to a porous or non-porous solvent insoluble material. Porous materials include paper, synthetic filters etc. In such porous materials, the reaction may take place within the pores. The support can have any one of a number of shapes, such as pin, strip, plate, disk, rod, bends, cylindrical structure, particle, including bead, nanoparticles and the like. The support can have variable widths. The support can be hydrophilic or capable of being rendered hydrophilic and includes inorganic powders such as silica, magnesium sulfate, and alumina; natural polymeric materials, particularly cellulosic materials and materials derived from cellulose, such as fiber containing papers, e.g., filter paper, chromatographic paper, etc.; synthetic or modified naturally occurring polymers, such as nitrocellulose, cellulose acetate, poly(vinyl chloride), polyacrylamide, cross linked dextran, agarose, polyacrylate, polyethylene, polypropylene, poly(4-methylbutene), polystyrene, polymethacrylate, poly(ethylene terephthalate), nylon, poly(vinyl butyrate), polyvinylidene difluoride (PVDF) membrane, glass, controlled pore glass, magnetic controlled pore glass, ceramics, metals, and the like etc.; either used by themselves or in conjunction with other materials. In some embodiments, oligonucleotides are synthesized in an array format. For example, single-stranded oligonucleotides are synthesized in situ on a common support, wherein each oligonucleotide is synthesized on a separate or discrete feature (or spot) on the substrate. In preferred embodiments, single-stranded oligonucleotides are bound to the surface of the support or feature. As used herein the term "array" refers to an arrangement of discrete features for storing, amplifying and releasing oligonucleotides or complementary oligonucleotides for further reactions. In a preferred embodiment, the support or array is addressable: the support includes two or more discrete addressable features at a particular predetermined location (i.e., an "address") on the support. Therefore, each oligonucleotide molecule on the array is localized to a known and defined location on the support. The sequence of each oligonucleotide can be determined from its position on the support. The array may comprise interfeatures regions. Interfeatures may not carry any oligonucleotide on their surface and may correspond to inert space.

The support may comprise at least 100, at least 1,000, at least $10^4$, at least $10^5$, at least $10^6$, at least $10^7$, at least $10^8$ features. In some embodiments, the oligonucleotides are covalently attached to the support. In some embodiments, each feature of the solid surface comprises a high density of oligonucleotides having a different predetermined sequence (e.g., approximately $10^6$-$10^8$ molecules per feature).

Parsing

In some embodiments, a nucleic acid sequence of interest can be parsed into a set of construction oligonucleotides that together comprise the nucleic acid sequence of interest. For example, in a first step, sequence information can be obtained. The sequence information may be the sequence of a nucleic acid of interest that is to be assembled.

In some embodiments, the sequence information may be analyzed to determine an assembly strategy, according to one or more of the following: the number of the junctions, the length of the junctions, the sequence of the junctions, the number of the fragments, the length of the fragments, the sequence of the fragments to be assembled e.g., by cohesive end ligation, to generate the predefined nucleic acid sequences of interest. In some embodiments, the fragments can be assembled by cohesive end ligation or by polymerase chain assembly.

In some embodiments, the assembly design is based on the length of the construction oligonucleotides and/or the number of junctions. In some embodiments, the design that results in the smaller number of fragments or junctions can be selected.

In some embodiments, the sequence analysis may involve scanning for the presence of one or more interfering sequence features that are known or predicted to interfere with oligonucleotide synthesis, amplification or assembly. For example, an interfering sequence structure may be a sequence that has a low GC content (e.g., less than 30% GC, less than 20% GC, less than 10% GC, etc.) over a length of at least 10 bases (e.g., 10-20, 20-50, 50-100, or more than 100 bases), or sequence that may be forming secondary structures or stem-loop structures.

Oligonucleotide Synthesis

It is understood that protocols known in the art for oligonucleotide synthesis may be used in the present invention. For example, the phosphoramidite method which employs nucleotides modified with various protecting groups may be used. Detailed procedures for the phosphoramidite and hydrogen phosphonate methods of oligonucleotide synthesis are described in the following references that are incorporated by reference: U.S. Pat. Nos. 4,500,707; 4,725,677; and 5,047,524. See also for example, methods outlined in Oligonucleotide and Analogs: A practical approach, F. Eckstein, Ed. IRL Press Oxford University and Oligonucleotide synthesis: A practical approach, Gait, Ed. IRL Oxford Press. Synthesis can be performed either through the coupling of the 5' position of the first monomer to the 3' position of the second monomer (3'-5' synthesis) or vice versa (5'-3' synthesis). Briefly, synthesis of oligonucleotides requires the specific formation of a 3'-5' or 5'-3' phosphodiester linkage. In order to form these specific linkages, the nucleophilic centers not involved in the linkage must be chemically protected through the use of protecting group. By "protecting group" as used herein is meant a species which prevents a segment of a molecule (e.g. nucleotide) from undergoing a specific chemical reaction, but which is removable from the molecule following completion of that reaction. For example, the 5' hydroxyl group may be protected by dimethoxitrityl (DMT). During the deblocking reaction, the DMT is removed with an acid, such as thrichloroacetic acid (TCA) or dichloroacetic acid, resulting in a free hydroxyl group. After washing, a phosphoramidite nucleotide is activated by tetrazole, ethylthiotetrazole, dicyanoimidazole, or benzimidazolium triflate, for example, which remove the iPr2N group on the phosphate group. The deprotected 5' hydroxyl of the first base reacts with the phosphate of the second base and a 5'-3' linkage is formed (coupling step). Unbound bases are washed out and 5' hydroxyl groups that did not react during the coupling reaction are blocked by adding a capping group, which permanently binds to the free 5' hydroxyl groups to prevent any further chemical transformation of that group (capping step). The oxidation step may be performed before or after the capping step. During oxidation, the phosphite linkage is stabilized to form a much more stable phosphate linkage. The deblocking/coupling/capping/oxidation cycle may be repeated the requisite number of time to achieve the desired length polynucleotide.

One skilled in the art would understand that to build an oligonucleotide of a particular length, a plurality of synthetic cycles is necessary. A synthetic cycle is repeated to add one monomer (e.g. nucleoside monomer unit) at a time to achieve the desired predefined sequence and length which define the oligonucleotide (e.g. oligonucleotide comprising X nucleotides).

In some embodiments, libraries of oligonucleotides are synthesized. In some embodiments, at least 100, at least 1000, at least 10,000, at least 100,000, at least $10^6$ or more oligonucleotides can be synthesized on a single array.

Some aspects the invention relate to the design of oligonucleotides for the high fidelity polynucleotide assembly. Aspects of the invention may be useful to increase the throughput rate of a nucleic acid assembly procedure and/or reduce the number of steps or amounts of reagent used to generate a correctly assembled nucleic acid sequence having a predefined sequence. Aspects of the invention may be useful in the context of automated nucleic acid assembly to reduce the time, number of steps, amount of reagents, and other factors required for the assembly of each correct nucleic acid sequence. Accordingly, these and other aspects of the invention may be useful to reduce the cost and time of one or more nucleic acid assembly procedures.

In exemplary embodiments, a compositions of synthetic oligonucleotides contains at least about 1%, 2%, 3%, 4%, 5%, 6%, 7%, 8%, 9%, 10%, 15%, 20%, 25%, 50%, 60%, 70%, 80%, 90%, 95% or more, copies that are error free (e.g., having a sequence that does not deviate from a predetermined sequence). The percent of error-free copies is based on the number of error-free copies in the composition as compared to the total number of copies of the polynucleotide in the composition that were intended to have the correct, e.g., predefined or predetermined sequence.

In some embodiments, pluralities of different single-stranded oligonucleotides are synthesized at different features of a solid support. In some embodiments, the support-bound oligonucleotides may be attached through their 5' end. In some embodiments, the support-bound oligonucleotides are attached through their 3' end. In some embodiments, the support-bound oligonucleotides may be immobilized on the support via a nucleotide sequence (e.g. degenerate binding sequence), linker or spacer (e.g. photocleavable linker or chemical linker). It should be appreciated that by 3' end, it is meant the sequence downstream to the 5' end and by 5' end it is meant the sequence upstream to the 3' end. For example, an oligonucleotide may be immobilized on the support via a nucleotide sequence, linker or spacer that is not involved in hybridization. The 3' end sequence of the support-bound oligonucleotide referred then to a sequence upstream to the linker or spacer.

Some aspects of the invention relate to compositions useful for the in situ synthesis of a plurality of oligonucleotides having a predefined sequence onto a support. Other aspects of the invention relate to a device for synthesizing a plurality of oligonucleotides having a predetermined sequence on a solid support. In some aspects of the invention, the compositions described herein are particularly useful for fabricating an addressable oligonucleotides array by in situ synthesis of oligonucleotides on a solid support. In one such embodiment, at each of the multiple different addresses on the support, the in situ synthesis steps may be repeated so as to form a support comprising a plurality of oligonucleotides (e.g. same or different oligonucleotide sequences) at one or more different addresses on the support. In some embodiments, the compositions of the invention are deposited as droplets at those addresses using, for example, a pulse jet printing system. The oligonucleotides can be synthesized by disposing solutions on the entire solid support (e.g. array) or at particular addressable features or spots of the solid support in a specific order in an iterative process.

It should be appreciated that oligonucleotides synthesized on arrays (e.g. microchips) are generally synthesized via chemical reactions. Spurious chemical reactions cause random base errors in oligonucleotides. A sequence error may include one or more nucleotide deletions, additions, substitutions (e.g., transversion or transition), inversions, duplications, or any combination of two or more thereof. One of the critical limitations in chemical nucleic acid synthesis is the error-rate. The error rate of chemically-synthesized oligonucleotides (e.g. deletions at a rate of 1 in 100 bases and mismatches and insertions at about 1 in 400 bases) exceeds the error rate obtainable through enzymatic means of replicating an existing nucleic acid (e.g., PCR).

Oligonucleotide Design and Array Design

According to some embodiments, the array can be designed to be redundant such that the oligonucleotides having the predefined sequence are repeated a plurality of times on the solid support. According to some embodiments, and as described herein, the oligonucleotides having the predefined sequence can comprise a central oligonucleotide sequence of interest, a 5' oligonucleotide flanking sequence and a 3' oligonucleotide flanking sequence (referred herein as flanking sequences). As used herein, the terms "central oligonucleotide sequence", "oligonucleotide of interest", "construction oligonucleotide" and "payload" are used interchangeably. One of skill in the art will appreciate that several levels of redundancy can be built into the array. Referring to an oligonucleotide of interest, there are at least two types of redundancy that can be built into an array. In a first level of redundancy, each oligonucleotide comprising the oligonucleotide of interest can be represented N times at N different features of the array. In a second level of redundancy, each oligonucleotide comprising the oligonucleotide of interest can be different from the other and designed to comprise an identical oligonucleotide of interest. In a third level of redundancy, each oligonucleotide of interest can be represented as two sets of oligonucleotides, the second set of oligonucleotides being a reverse complement of the first set of oligonucleotides. Building redundancy into an array can give several significant advantages, including robustness of the array and the ability to produce oligonucleotides of interest having the predefined sequence, i.e. oligonucleotides that are substantially error-free.

It should be appreciated that redundancy can be helpful in synthesizing oligonucleotides without localized errors. According to some aspects of the invention, the methods of the invention use combinatorial chemistry on a solid support within a flow chamber. Since the oligonucleotides on the support are synthesized within a global environment, fluid flow error can cause global errors and affect all oligonucleotides on a per-cycle (or per-nucleotide addition) context. In this context, the first level of redundancy may not protect against errors if the array undergoes a global error process, for example, a fluid flow error, since all redundant oligonucleotides are locked in the same nucleotide addition phase. In some embodiments, by introducing a plurality of padding sequences having different lengths upstream to each desired construction oligonucleotide sequence (or payload), a nucleotide phased shift may be introduced during the oligonucleotide synthesis. Such designs described herein have the advantage not affect the downstream content of the oligonucleotide sequence of interest and not to affect redundancy. The shift in cycle time can help mitigate global synthesis cycle events from causing errors in the downstream nucleic acid assembly.

According to some aspects of the invention, the oligonucleotides to be synthesized are designed so as to have an additional sequence (also referred herein as padding sequence) upstream a sequence of interest. In some embodiments, a synthetic oligonucleotide may include a central sequence flanked by 5' and 3' amplification sequences. The flanking sequences are designed for amplification and are not intended to be part of the final oligonucleotide sequence or incorporated into the assembled nucleic acid. The flanking amplification sequences may be used as primer sequences to amplify a plurality of different assembly oligonucleotides that share the same amplification sequences but have different central assembly sequences. In some embodiments, the flanking sequences are removed after amplification to produce an oligonucleotide that contains only the assembly sequence.

Figure 1A:
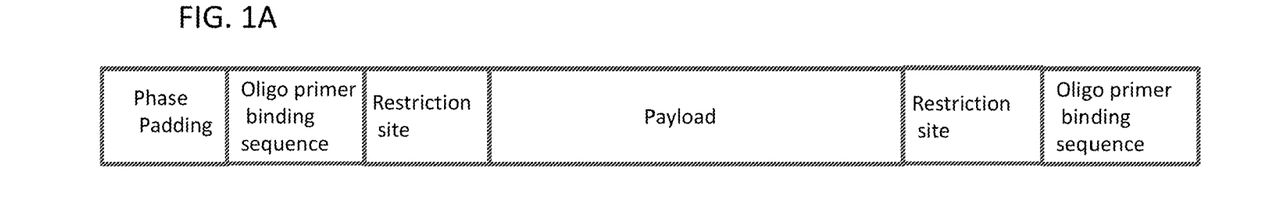
FIG. 1A illustrates a first exemplary design of oligonucleotides for synthesis according to a non-limiting embodiment.
Figure 1B:
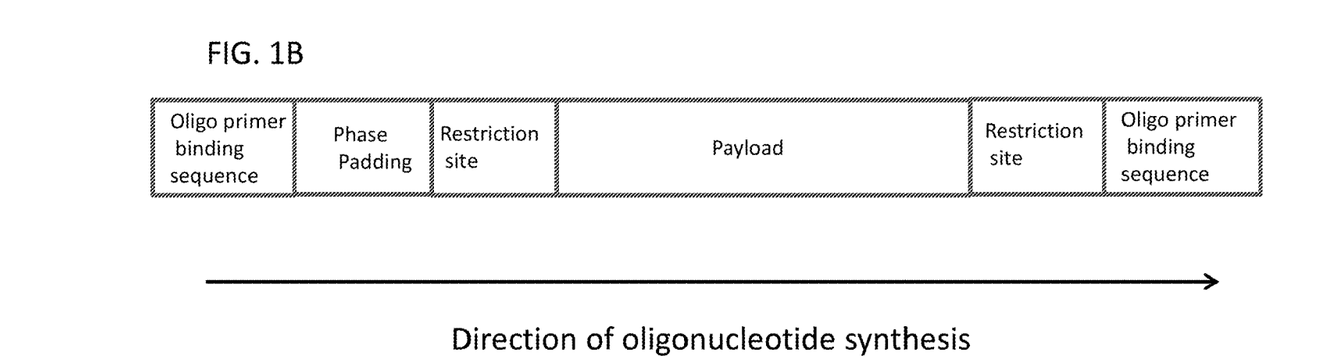
FIG. 1B illustrates a second exemplary design of oligonucleotides for synthesis according to a non-limiting embodiment.

FIG. 1B shows an exemplary composition comprising an oligonucleotide comprising from the 5' end to the 3' end: an oligonucleotide primer binding sequence (also referred herein as primer binding site), a set of padding nucleotides (also referred herein as phased padding), a restriction enzyme recognition sequence (also referred herein as restriction site), a set of specific nucleotides making up the construction oligonucleotide having a predefined sequence (also referred herein as payload), a restriction enzyme sequence, and an oligonucleotide primer binding sequence. Yet in other embodiments, the padding sequence can be upstream the primer sequence (see FIG. 1A) or directly upstream the payload sequence. In this oligonucleotide design, the primers binding sequences allow amplification and the recognition sites for the restriction enzyme(s) allow the primer binding sequences to be cleaved off from the payload.

In some embodiments, the oligonucleotide sequences may be designed to include: amplification primer sequence(s), padding, recognition site for a restriction enzyme, such as a type IIS restriction enzyme, payload, recognition site for a restriction enzyme (same or different restriction enzyme), and amplification primer sequence(s). The terms "amplification primer sequence", "primer binding site", "primer binding sequence" and "primer recognition site" are used interchangeably. In other embodiments, the oligonucleotide sequences can may be designed to include: padding, amplification primer sequence(s), recognition site for a restriction enzyme, such as a type IIS restriction enzyme, payload, recognition site for a restriction enzyme (same or different restriction enzyme), and amplification primer sequence. In some embodiments, the payload can be an overlapping subset of a target gene to be assembled (or any arbitrary nucleic acid sequence).

In various embodiments, the construction oligonucleotide is padded upstream with a padding sequence of (m) nucleotides M ($M_m$). In some embodiments, the construction oligonucleotide is padded at the 3' end with a padding sequence of (m) nucleotides M ($M_m$). In some embodiments, for each construction oligonucleotide, a plurality of oligonucleotides comprising the construction oligonucleotide can be synthesized, each construction oligonucleotide being padded with a padding sequence having a different length. In some embodiments, the padding sequence can be 4 bases long, 5 bases long, 6 bases long, 7 bases long, 8 bases long, 9 bases long, or 10 bases long or longer. For example, each payload can be padded so as to add at least 4 bps upstream the payload sequence. In an exemplary embodiment, each oligonucleotide (O1, O2, . . . On) designed to have an identical construction oligonucleotide sequence or payload p1 is synthesized at n different features of the array. The oligonucleotides O1, O2, . . . and On can be designed to have different length of padding sequences. It should be appreciated that to achieve array redundancy, n is at least 2. In some embodiments, the set of padding nucleotides is composed of (m) degenerate bases N. Yet in other embodiments, the padding sequence is designed not to interfere with the payload sequence. For example, the padding sequence can be designed not to include repeated sequences, sequences having a significantly high or low GC content, sequences associated with secondary structures and/or sequences capable of hybridizing with the central oligonucleotide sequence.

According to some aspects of the invention, a redundant array designed to have two or more pluralities of oligonucleotides is provided, each of the plurality of oligonucleotides comprising a different construction oligonucleotide. In some embodiments, each oligonucleotide of each plurality of oligonucleotides comprises an identical construction oligonucleotide sequence and differ in length from each other. In some embodiments, each oligonucleotide of each plurality of oligonucleotides has a 5' flanking sequence, each 5' flanking sequence being different from each other. In some embodiments, the 5' flanking sequences can differ in length.

In certain embodiments, the payload or central sequence may be designed to have a sequence that is identical to a different portion of the sequence of a predetermined target nucleic acid that is to be assembled. Accordingly, in some embodiments each oligonucleotide may have a sequence that is identical to a portion of one of the two strands of a double-stranded target nucleic acid. For clarity, the two complementary strands of a double stranded nucleic acid are referred to herein as the positive (P) and negative (N) strands. This designation is not intended to imply that the strands are sense and anti-sense strands of a coding sequence. They refer only to the two complementary strands of a nucleic acid (e.g., a target nucleic acid, an intermediate nucleic acid fragment, etc.) regardless of the sequence or function of the nucleic acid. Accordingly, in some embodiments a P strand may be a sense strand of a coding sequence, whereas in other embodiments a P strand may be an anti-sense strand of a coding sequence. It should be appreciated that the reference to complementary nucleic acids or complementary nucleic acid regions herein refers to nucleic acids or regions thereof that have sequences which are reverse complements of each other so that they can hybridize in an antiparallel fashion typical of natural DNA.

According to some embodiments, a method of mitigating both local and global error events can include synthesizing both the forward and reverse strands on the same array. Such design allows for the production of two different species for the same downstream molecule, increasing the overall redundancy. If the forward strand, for example, is defective, a correct representation of the sequence can be built using PCR from the reverse strand. According to some embodiments, each internal sequence can be represented by two sets of oligonucleotides, the second set being a reverse complement of the first set of oligonucleotide (i.e. the forward oligonucleotide).

There are several different ways to take advantage of allocating multiple spots to each oligonucleotide of a construct. In some embodiments, the construct can be parsed in at least two different ways, and the available two or more spots are allocated among the different parses. In some embodiments, the different parses can start from the 5' end and separately from the 3'end or can start at the actual beginning and at an offset after the inserted padding. It should be appreciated that changing the parse can alter junctions, the secondary structure of the oligonucleotides, the GC content of the oligonucleotides and other features, and can affect the synthesis and/or assembly yield. An alternate parse may also intentionally or incidentally disrupt long homopolymer runs and/or the recognition site for restriction enzymes. Because of the complex interactions inherent in biology, it should be appreciated that it is not always possible to predict informatically (algorithmically) which parse may yield better results. In some embodiments, it can be advantageous to try multiple parses, on the same support or array.

According to various embodiments, the allocating multiple spots, the default allocation may be uniform. For example, half the spots on the array may be allocated for the forward oligonucleotides and half the spots on the array may be allocated for the reverse complement oligonucleotides. In some embodiments, the methods may be combined, e.g. one-fourth of the spots each for: forward oligonucleotide of 5' parse, reverse complement oligonucleotide of 5' parse, forward oligonucleotide of 3' parse, reverse complement of 3' parse.

However, if there is any reason to predict (or metrics to indicate) that one set of the parsed results may be more difficult to synthesize on the array, or to assemble or otherwise make use of after array synthesis, the spots may also be allocated in non-uniform fashion. For example, a 'G' may be more prone to synthesis problems, so the forward or reverse complement that has fewer Gs could be included more frequently (e.g. ⅔ or ¾ of the available spots), while including some of the other strand to gain the benefit of diversity.

In some embodiments, by adding artificial padding to the start of a gene, a shift that forces the parse to generate different (shifted) oligonucleotides can be created. In some embodiments, the padding can be at the 5' end or the 3' end of the sequence of interest.

When designing an array, any number of the methods described herein can be computationally selected and combined to balance the pool complexity. For example, a given array might have a high number of constructs that can prevent alternative parses, but can have enough capacity to allocate spots for the forward and the reverse complement strand in four different phases.

In some embodiments, oligonucleotides can be eluted from the microarray prior to be subjected to amplification or can be amplified on the microarray. In some embodiments, the oligonucleotides can be designed such as having at their 3' and 5' end a primer binding sequence and the oligonucleotides can be amplified by polymerase chain reaction (PCR) using suitable primers.

In some embodiments, oligonucleotides may be amplified using an appropriate primer pair with one primer corresponding to each end of the oligonucleotide (e.g., one that is complementary to the 3' end of the oligonucleotide and one that is identical to the 5' end of the oligonucleotide). In some embodiments, an oligonucleotide may be designed to contain a central assembly sequence (designed for incorporation into an assembled nucleic acid, also referred herein as payload) flanked by a 5' amplification sequence (e.g., a 5' universal sequence or 5' common amplification sequence) and a 3' amplification sequence (e.g., a 3' universal sequence or 5' common amplification sequence).

Amplification primers (e.g., between 10 and 50 nucleotides long, between 15 and 45 nucleotides long, about 25 nucleotides long, etc.) corresponding to the flanking amplification sequences may be used to amplify the oligonucleotide (e.g., one primer may be complementary to the 3' amplification sequence and one primer may have the same sequence as the 5' amplification sequence). In some embodiments, a plurality of different oligonucleotides (e.g., about 5, 10, 50, 100, or more) with different central assembly sequences may have identical 5' amplification sequences and identical 3' amplification sequences. These oligonucleotides can all be amplified in the same reaction using the same amplification primers. The amplification sequences may then be removed from the amplified oligonucleotide using any suitable technique to produce an oligonucleotide that contains only the assembly sequence. In some embodiments, the amplification sequences are removed by a restriction enzyme as described in more details herein.

In some embodiments, the oligonucleotides may be amplified while it is still attached to the support. In some embodiments, the oligonucleotides may be removed or cleaved from the support prior to amplification.

In some embodiments, the oligonucleotides are designed to have a restriction site. In some embodiments, the restriction site can be a Type IIS restriction site. Type IIS restriction enzymes are enzymes that bind to a double stranded nucleic acid at one site, referred to as the recognition site, and make a single double stranded cut outside of the recognition site. The double stranded cut, referred to as the cleavage site, is generally situated 0-20 bases away from the recognition site. The recognition site is generally about 4-7 bps long. All type IIS restriction enzymes exhibit at least partial asymmetric recognition. Asymmetric recognition means that 5'3' recognition sequences are different for each strand of the nucleic acid. The enzyme activity also shows polarity meaning that the cleavage sites are located on only one side of the recognition site. Thus, there is generally only one double stranded cut corresponding to each recognition site. Cleavage generally produces 1-5 nucleotide single-stranded overhangs, with 5' or 3' termini, although some enzymes produce blunt ends. Either cut is useful in the context of the invention, although in some instances those producing single-stranded overhangs are produced. To date, about 80 type IIS enzymes have been identified. Examples include but are not limited to BstF5 I, BtsC I, BsrD I, Bts I, Alw I, Bcc I, BsmA I, Ear I, Mly I (blunt), Ple I, Bmr I, Bsa I, BsmB I, Fau I, Mnl I, Sap I, Bbs I, BciV I, Hph I, Mbo II, BfuA I, BspCN I, BspM I, SfaN I, Hga I, BseR I, Bbv I, Eci I, Fok I, BceA I, BsmF I, BtgZ I, BpuE I, Bsg I, Mme I, BseG I, Bse3D I, BseM I, AcIW I, Alw26 I, Bst6 I, BstMA I, Eam1104 I, Ksp632 I, Pps I, Sch I (blunt), Bfi I, Bso31 I, BspTN I, Eco31 I, Esp3 I, Smu I, Bfu I, Bpi I, BpuA I, BstV2 I, AsuHP I, Acc36 I, Lwe I, Aar I, BseM II, TspDT I, TspGW I, BseX I, BstV1 I, Eco57 I, Eco57M I, Gsu I, and Bcg I. Such enzymes and information regarding their recognition and cleavage sites are available from commercial suppliers such as New England BioLabs, Inc. (Ipswich, Mass., U.S.A.).

In some embodiments, commercial or engineered restriction enzyme may be used. In some embodiments, Type IIS restriction enzymes can be designed and engineered to produce longer overhang lengths. Designing and engineering restriction enzymes to produce longer single-stranded overhangs can allow for the joining of a larger number of oligonucleotides together to form longer nucleic acid constructs. For example, BsaI, which produces a 4 nucleotide single-stranded overhang, can be engineered to produce a 5, or 6 or longer single-stranded overhang. Increasing the length of the single-stranded overhang produced by such engineered BsaI can increase the theoretical limit of 17 nucleic acids or oligonucleotides that can be joined.

In some embodiments, each of a plurality of oligonucleotides designed for nucleic acid assembly may have a type IIS restriction site at each end. The type IIS restriction sites may be oriented so that the cleavage sites are internal relative to the recognition sequences. As a result, enzyme digestion exposes an internal sequence (e.g., an overhang within an internal sequence) and removes the recognition sequences from the ends. Accordingly, the same type IIS sites may be used for both ends of all of the nucleic acid fragments being prepared for assembly and/or may be used for linearizing a suitable vector. However, different type IIS sites also may be used. Two fragments that are designed to be adjacent in an assembled product each may include an identical overlapping terminal sequence and a flanking type IIS site that is appropriately located to expose complementary overhangs within the overlapping sequence upon restriction enzyme digestion. Accordingly, a plurality of nucleic acid fragments may be generated with different complementary overhangs. The restriction site at each end of a nucleic acid fragment may be located such that digestion with the appropriate type IIS enzyme removes the restriction site and exposes a single-stranded region that is complementary to a single-stranded region on a nucleic acid fragment that is designed to be adjacent in the assembled nucleic acid product. In some embodiments, one end of each of the two terminal nucleic acid fragments may be designed to have a single-stranded overhang (e.g., after digestion with an appropriate restriction enzyme) that is complementary to a single-stranded overhang of a linearized vector nucleic acid. Accordingly, the resulting nucleic acid fragments and vector may be transformed directly into a host cell. Alternatively, the nucleic acid fragments and vector may be incubated to promote hybridization and annealing of the complementary sequences prior to transformation in the host cell. It should be appreciated that a vector may be prepared using any one of the techniques described herein or any other suitable technique that produces a single-stranded overhang that would be complementary to an end of one of the terminal nucleic acid fragments.

Amplifying Oligonucleotides

Oligonucleotides may be provided or synthesized as single-stranded synthetic products. In some embodiments, oligonucleotides may also be provided or synthesized as double-stranded preparations including an annealed complementary strand. Oligonucleotides may be molecules of DNA, RNA, PNA, or any combination thereof. A double-stranded oligonucleotide may be produced by amplifying a single-stranded synthetic oligonucleotide or other suitable template (e.g., a sequence in a nucleic acid preparation such as a nucleic acid vector or genomic nucleic acid). Accordingly, a plurality of oligonucleotides designed to have the sequence features described herein may be provided as a plurality of single-stranded oligonucleotides having those features, or also may be provided along with complementary oligonucleotides. In some embodiments, an oligonucleotide may be phosphorylated (e.g., with a 5' phosphate). In some embodiments, an oligonucleotide may be non-phosphorylated.

In some embodiments, an oligonucleotide may be amplified using an appropriate primer pair with one primer corresponding to each end of the oligonucleotide (e.g., one that is complementary to the 3' end of the oligonucleotide and one that is identical to the 5' end of the oligonucleotide). In some embodiments, an oligonucleotide may be designed to contain a central assembly sequence (designed to be incorporated into the target nucleic acid) flanked by a 5' amplification sequence (e.g., a 5' universal sequence) and/or a 3' amplification sequence (e.g., a 3' universal sequence). Amplification primers (e.g., between 10 and 50 nucleotides long, between 15 and 45 nucleotides long, about 25 nucleotides long, etc.) corresponding to the flanking amplification sequences may be used to amplify the oligonucleotide (e.g., one primer may be complementary to the 3' amplification sequence and one primer may have the same sequence as the 5' amplification sequence). The amplification sequences then may be removed from the amplified oligonucleotide using any suitable technique to produce an oligonucleotide that contains only the assembly sequence.

In some embodiments, a plurality of different oligonucleotides (e.g., about 5, 10, 50, 100, or more) with different central assembly sequences may have identical 5' amplification sequences and/or identical 3' amplification sequences. These oligonucleotides can all be amplified in the same reaction using the same amplification primers.

A plurality of oligonucleotides used in an assembly reaction may contain preparations of synthetic oligonucleotides, single-stranded oligonucleotides, double-stranded oligonucleotides, amplification products, oligonucleotides that are processed to remove (or reduce the frequency of) error-containing variants, etc., or any combination of two or more thereof. In some aspects, double-stranded amplification products may be used as assembly oligonucleotides and added to an assembly reaction as described herein. In some embodiments, the oligonucleotides may be amplified while they are still attached to the support. In some embodiments, the oligonucleotides may be removed or cleaved from the support prior to amplification or after amplification.

In some embodiments, a synthetic oligonucleotide may include a central assembly sequence flanked by 5' and 3' amplification sequences. The central assembly sequence is designed for incorporation into an assembled target nucleic acid or target subassembly. The flanking sequences are designed for amplification and are not intended to be incorporated into the assembled nucleic acid. The flanking amplification sequences may be used as universal primer sequences to amplify a plurality of different assembly oligonucleotides that share the same amplification sequences but have different central assembly sequences. In some embodiments, the flanking sequences are removed after amplification to produce an oligonucleotide that contains only the assembly sequence.

In certain embodiments, the double-stranded amplification products may be subjected to restriction enzyme digestion to remove the flanking sequences. To that end, the flanking sequences can be designed to include one or more restriction sites or restriction enzyme recognition sites. The restriction site may be present at the 5' or 3' end of the amplification sequence as long as the cleavage site is between the flanking sequence to be removed and the central assembly sequence. The restriction site may be included in the amplification sequence (i.e., primer binding site). The restriction site may also be outside the amplification sequence.

After restriction enzyme digestion, the cleaved flanking sequences may be separated and removed using any suitable technique. In some embodiments, the cleaved flanking sequences may be fragments less than about 40, about 35, about 30, about 25, about 20, or about 15 bases long. As such, size dependent separation techniques known in the art may be used, such as differential affinity to silica, size filtration, differential precipitation with PEG (polyethylene glycol) or CTAB (cetyltrimethlyammonium bromide), or any combination thereof, so as to separate the cleaved flanking sequences from the central assembly sequences that can be designed to be longer in size than the flanking sequences.

In some embodiments, the amplification primers may be biotinylated. The resulting amplification products thus also become biotinylated at both ends. Upon restriction enzyme digestion, the cleaved flanking sequences having the biotinylated primers retain the biotin tags, while the central assembly sequences are non-biotinylated. Thus, the cleaved flanking sequences can be affinity purified and removed using streptavidin (e.g., bound to a bead, column, or other surface). In some embodiments, the amplification primers also may be designed to include certain sequence features (e.g., restriction sites) that can be used to remove the primer regions after amplification in order to produce a double-stranded assembly fragment that includes the assembly sequence without the flanking amplification sequences.

Error Reduction

In some embodiments, one or more oligonucleotide preparations may be subjected to an error reduction or error filtration process to remove (or reduce the number or the frequency of) error-containing oligonucleotides. Such process can be used to increase the number of error-free oligonucleotides in the oligonucleotide preparations. Methods for conducting error reduction or error filtration can include, for example, hybridization to a selection oligonucleotide, binding to a mismatch binding agent or to a mismatch binding protein or combinations thereof.

In some embodiments, error correction may be included after oligonucleotide synthesis and/or at the end of the assembly process to increase the relative population of synthesized polynucleotides without deviation from the desired sequences. Such error correction may include direct sequencing and/or the application of error correcting enzymes such as error correcting nucleases (e.g. CEL I, CELII), error correction based on MutS or MutS homologs binding or other mismatch binding proteins, other means of error correction as known in the art or any combination thereof. In some embodiments, MutS or homologs thereof or CEL I or CELII may be added to the oligonucleotide duplexes in solution. CEL I or CEL II is a mismatch specific endonuclease that cleaves all types of mismatches such as single nucleotide polymorphisms, small insertions or deletions. Addition of the CE endonuclease results in the cleavage of the double-stranded oligonucleotides at the site or region of the mismatch. In some embodiments, MutS, a MutS homolog, or a combination thereof can be used to bind to heteroduplex molecules. MutS from *Thermus aquaticus* can be purchase commercially from the Epicenter Corporation, Madison, Wis., Catalog No. SP72100 and SP72250. The gene sequence for the protein is also known and published in Biswas and Hsieh, Jour. Biol. Chem. 271:5040-5048 (1996) and is available in GenBank, accession number U33117. In *E. coli*, the MutS protein, which appears to function as a homodimer, serves as a mismatch recognition factor. In eukaryotes, at least three MutS Homolog (MSH) proteins have been identified; namely, MSH2, MSH3, and MSH6, and they form heterodimers. For example in the yeast, *Saccharomyces cerevisiae*, the MSH2-MSH6 complex (also known as MutSα) recognizes base mismatches and single nucleotide insertion/deletion loops, while the MSH2-MSH3 complex (also known as MutSβ) recognizes insertions/deletions of up to 12-16 nucleotides, although they exert substantially redundant functions. A mismatch binding protein may be obtained from recombinant or natural sources. A mismatch binding protein may be heat-stable. In some embodiments, a thermostable mismatch binding protein from a thermophilic organism may be used. Examples of thermostable DNA mismatch binding proteins include, but are not limited to: Tth MutS (from *Thermus thermophilus*); Taq MutS (from *Thermus aquaticus*); Apy MutS (from *Aquifex pyrophilus*); Tma MutS (from *Thermotoga maritima*); any other suitable MutS; or any combination of two or more thereof.

In some embodiments, the synthetic oligonucleotides having the desired or predetermined sequence are sorted by isolating clonal populations of nucleic acids, determining the sequence of the clonal populations and isolating the clonal population having the predefined sequence or as described in U.S. Provisional Application Ser. No. 61/848,961, filed Jan. 16, 2013, and U.S. application Ser. No. 13/986,366, filed Mar. 24, 2013, which are incorporated herein by reference in their entirety.

Applications

Aspects of the invention may be useful for a range of applications involving the production and/or use of synthetic nucleic acids. As described herein, the invention provides methods for synthesizing synthetic nucleic acids. Some aspects of the invention relate to a gene synthesis platform using methods described herein. In some embodiments, the gene synthesis platform can be combined with a next generation sequencing platform (e.g. sequencing by hybridization, sequencing by synthesis, sequencing by ligation or any other suitable sequencing method.

In some embodiments, the assembly procedure may include several parallel and/or sequential reaction steps in which a plurality of different nucleic acids or oligonucleotides are synthesized or immobilized, amplified, and are combined in order to be assembled (e.g., by extension or by ligation as described herein) to generate a longer nucleic acid product to be used for further assembly, cloning, or other applications (see PCT application PCT/US09/55267 which is incorporate herein by reference in its entirety).

The resulting assembled nucleic acids may be amplified in vitro (e.g., using PCR, LCR, or any suitable amplification technique), amplified in vivo (e.g., via cloning into a suitable vector), isolated and/or purified. An assembled nucleic acid (alone or cloned into a vector) may be transformed into a host cell (e.g., a prokaryotic, eukaryotic, insect, mammalian, or other host cell). In some embodiments, the host cell may be used to propagate the nucleic acid. In certain embodiments, the nucleic acid may be integrated into the genome of the host cell. In some embodiments, the nucleic acid may replace a corresponding nucleic acid region on the genome of the cell (e.g., via homologous recombination). Accordingly, nucleic acids may be used to produce recombinant organisms. In some embodiments, a target nucleic acid may be an entire genome or large fragments of a genome that are used to replace all or part of the genome of a host organism. Recombinant organisms also may be used for a variety of research, industrial, agricultural, and/or medical applications.

Many of the techniques described herein can be used together, applying suitable assembly techniques at one or more points to produce long nucleic acid molecules. For example, ligase-based assembly may be used to assemble oligonucleotide duplexes and nucleic acid fragments of less than 100 to more than 10,000 base pairs in length (e.g., 100 mers to 500 mers, 500 mers to 1,000 mers, 1,000 mers to 5,000 mers, 5,000 mers to 10,000 mers, 25,000 mers, 50,000 mers, 75,000 mers, 100,000 mers, etc.). In an exemplary embodiment, methods described herein may be used during the assembly of an entire genome (or a large fragment thereof, e.g., about 10%, 20%, 30%, 40%, 50%, 60%, 70%, 80%, 90%, or more) of an organism (e.g., of a viral, bacterial, yeast, or other prokaryotic or eukaryotic organism), optionally incorporating specific modifications into the sequence at one or more desired locations.

Any of the nucleic acid products (e.g., including nucleic acids that are amplified, cloned, purified, isolated, etc.) may be packaged in any suitable format (e.g., in a stable buffer, lyophilized, etc.) for storage and/or shipping (e.g., for shipping to a distribution center or to a customer). Similarly, any of the host cells (e.g., cells transformed with a vector or having a modified genome) may be prepared in a suitable buffer for storage and or transport (e.g., for distribution to a customer). In some embodiments, cells may be frozen. However, other stable cell preparations also may be used.

Host cells may be grown and expanded in culture. Host cells may be used for expressing one or more RNAs or polypeptides of interest (e.g., therapeutic, industrial, agricultural, and/or medical proteins). The expressed polypeptides may be natural polypeptides or non-natural polypeptides. The polypeptides may be isolated or purified for subsequent use.

Accordingly, nucleic acid molecules generated using methods of the invention can be incorporated into a vector. The vector may be a cloning vector or an expression vector. In some embodiments, the vector may be a viral vector. A viral vector may comprise nucleic acid sequences capable of infecting target cells. Similarly, in some embodiments, a prokaryotic expression vector operably linked to an appropriate promoter system can be used to transform target cells. In other embodiments, a eukaryotic vector operably linked to an appropriate promoter system can be used to transfect target cells or tissues.

Transcription and/or translation of the constructs described herein may be carried out in vitro (i.e. using cell-free systems) or in vivo (i.e. expressed in cells). In some embodiments, cell lysates may be prepared. In certain embodiments, expressed RNAs or polypeptides may be isolated or purified. Nucleic acids of the invention also may be used to add detection and/or purification tags to expressed polypeptides or fragments thereof. Examples of polypeptide-based fusion/tag include, but are not limited to, hexa-histidine ($His^6$) Myc and HA, and other polypeptides with utility, such as $GFP_5$ GST, MBP, chitin and the like. In some embodiments, polypeptides may comprise one or more unnatural amino acid residue(s).

In some embodiments, antibodies can be made against polypeptides or fragment(s) thereof encoded by one or more synthetic nucleic acids. In certain embodiments, synthetic nucleic acids may be provided as libraries for screening in research and development (e.g., to identify potential therapeutic proteins or peptides, to identify potential protein targets for drug development, etc.) In some embodiments, a synthetic nucleic acid may be used as a therapeutic (e.g., for gene therapy, or for gene regulation). For example, a synthetic nucleic acid may be administered to a patient in an amount sufficient to express a therapeutic amount of a protein. In other embodiments, a synthetic nucleic acid may be administered to a patient in an amount sufficient to regulate (e.g., down-regulate) the expression of a gene.

It should be appreciated that different acts or embodiments described herein may be performed independently and may be performed at different locations in the United States or outside the United States. For example, each of the acts of receiving an order for a target nucleic acid, analyzing a target nucleic acid sequence, designing one or more starting nucleic acids (e.g., oligonucleotides), synthesizing starting nucleic acid(s), purifying starting nucleic acid(s), assembling starting nucleic acid(s), isolating assembled nucleic acid(s), confirming the sequence of assembled nucleic acid(s), manipulating assembled nucleic acid(s) (e.g., amplifying, cloning, inserting into a host genome, etc.), and any other acts or any parts of these acts may be performed independently either at one location or at different sites within the United States or outside the United States. In some embodiments, an assembly procedure may involve a combination of acts that are performed at one site (in the United States or outside the United States) and acts that are performed at one or more remote sites (within the United States or outside the United States).

Automated Applications

Aspects of the methods and devices provided herein may include automating one or more acts described herein. In some embodiments, one or more steps of an amplification and/or assembly reaction may be automated using one or more automated sample handling devices (e.g., one or more automated liquid or fluid handling devices). Automated devices and procedures may be used to deliver reaction reagents, including one or more of the following: starting nucleic acids, buffers, enzymes (e.g., one or more ligases and/or polymerases), nucleotides, salts, and any other suitable agents such as stabilizing agents. Automated devices and procedures also may be used to control the reaction conditions. For example, an automated thermal cycler may be used to control reaction temperatures and any temperature cycles that may be used. In some embodiments, a scanning laser may be automated to provide one or more reaction temperatures or temperature cycles suitable for incubating polynucleotides. Similarly, subsequent analysis of assembled polynucleotide products may be automated. For example, sequencing may be automated using a sequencing device and automated sequencing protocols. Additional steps (e.g., amplification, cloning, etc.) also may be automated using one or more appropriate devices and related protocols. It should be appreciated that one or more of the device or device components described herein may be combined in a system (e.g., a robotic system) or in a micro-environment (e.g., a micro-fluidic reaction chamber). Assembly reaction mixtures (e.g., liquid reaction samples) may be transferred from one component of the system to another using automated devices and procedures (e.g., robotic manipulation and/or transfer of samples and/or sample containers, including automated pipetting devices, micro-systems, etc.). The system and any components thereof may be controlled by a control system.

Accordingly, method steps and/or aspects of the devices provided herein may be automated using, for example, a computer system (e.g., a computer controlled system). A computer system on which aspects of the technology provided herein can be implemented may include a computer for any type of processing (e.g., sequence analysis and/or automated device control as described herein). However, it should be appreciated that certain processing steps may be provided by one or more of the automated devices that are part of the assembly system. In some embodiments, a computer system may include two or more computers. For example, one computer may be coupled, via a network, to a second computer. One computer may perform sequence analysis. The second computer may control one or more of the automated synthesis and assembly devices in the system. In other aspects, additional computers may be included in the network to control one or more of the analysis or processing acts. Each computer may include a memory and processor. The computers can take any form, as the aspects of the technology provided herein are not limited to being implemented on any particular computer platform. Similarly, the network can take any form, including a private network or a public network (e.g., the Internet). Display devices can be associated with one or more of the devices and computers. Alternatively, or in addition, a display device may be located at a remote site and connected for displaying the output of an analysis in accordance with the technology provided herein. Connections between the different components of the system may be via wire, optical fiber, wireless transmission, satellite transmission, any other suitable transmission, or any combination of two or more of the above.

Each of the different aspects, embodiments, or acts of the technology provided herein can be independently automated and implemented in any of numerous ways. For example, each aspect, embodiment, or act can be independently implemented using hardware, software or a combination thereof. When implemented in software, the software code can be executed on any suitable processor or collection of processors, whether provided in a single computer or distributed among multiple computers. It should be appreciated that any component or collection of components that perform the functions described above can be generically considered as one or more controllers that control the above-discussed functions. The one or more controllers can be implemented in numerous ways, such as with dedicated hardware, or with general purpose hardware (e.g., one or more processors) that is programmed using microcode or software to perform the functions recited above.

In this respect, it should be appreciated that one implementation of the embodiments of the technology provided herein comprises at least one computer-readable medium (e.g., a computer memory, a floppy disk, a compact disk, a tape, etc.) encoded with a computer program (i.e., a plurality of instructions), which, when executed on a processor, performs one or more of the above-discussed functions of the technology provided herein. The computer-readable medium can be transportable such that the program stored thereon can be loaded onto any computer system resource to implement one or more functions of the technology provided herein. In addition, it should be appreciated that the reference to a computer program which, when executed, performs the above-discussed functions, is not limited to an application program running on a host computer. Rather, the term computer program is used herein in a generic sense to reference any type of computer code (e.g., software or microcode) that can be employed to program a processor to implement the above-discussed aspects of the technology provided herein.

It should be appreciated that in accordance with several embodiments of the technology provided herein wherein processes are stored in a computer readable medium, the computer implemented processes may, during the course of their execution, receive input manually (e.g., from a user).

Accordingly, overall system-level control of the assembly devices or components described herein may be performed by a system controller which may provide control signals to the associated nucleic acid synthesizers, liquid handling devices, thermal cyclers, sequencing devices, associated robotic components, as well as other suitable systems for performing the desired input/output or other control functions. Thus, the system controller along with any device controllers together form a controller that controls the operation of a nucleic acid assembly system. The controller may include a general purpose data processing system, which can be a general purpose computer, or network of general purpose computers, and other associated devices, including communications devices, modems, and/or other circuitry or components to perform the desired input/output or other functions. The controller can also be implemented, at least in part, as a single special purpose integrated circuit (e.g., ASIC) or an array of ASICs, each having a main or central processor section for overall, system-level control, and separate sections dedicated to performing various different specific computations, functions and other processes under the control of the central processor section. The controller can also be implemented using a plurality of separate dedicated programmable integrated or other electronic circuits or devices, e.g., hard wired electronic or logic circuits such as discrete element circuits or programmable logic devices. The controller can also include any other components or devices, such as user input/output devices (monitors, displays, printers, a keyboard, a user pointing device, touch screen, or other user interface, etc.), data storage devices, drive motors, linkages, valve controllers, robotic devices, vacuum and other pumps, pressure sensors, detectors, power supplies, pulse sources, communication devices or other electronic circuitry or components, and so on. The controller also may control operation of other portions of a system, such as automated client order processing, quality control, packaging, shipping, billing, etc., to perform other suitable functions known in the art but not described in detail herein.

Various aspects of the present invention may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

EQUIVALENTS

The present invention provides among other things novel methods and devices for high-fidelity gene assembly. While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

INCORPORATION BY REFERENCE

All publications, patents and sequence database entries mentioned herein are hereby incorporated by reference in their entirety as if each individual publication or patent was specifically and individually indicated to be incorporated by reference. Reference is made to U.S. Provisional Application No. 61/851,759 filed Mar. 13, 2013, which is incorporated by reference in its entirety.

The invention claimed is:
1. A method for generating an oligonucleotide having a predefined sequence, the method comprising:
   a. designing at least one plurality of oligonucleotides, each oligonucleotide of each plurality of oligonucleotides having a different length and each oligonucleotide having an identical predefined internal sequence, a 3' flanking sequence at the 3' end of the internal sequence and a 5' flanking sequence at the 5' end of the internal sequence, wherein the 3' flanking sequence comprises a primer recognition site and a restriction enzyme recognition site;

wherein the 5' flanking sequence comprises a primer recognition site, a restriction enzyme recognition site and a padding nucleotide sequence, wherein each oligonucleotide of each plurality of oligonucleotides comprises a padding nucleotide sequence of a different length;

b. synthesizing the at least one plurality of oligonucleotides on a solid support; and c. isolating the oligonucleotide having the predefined sequence.

2. The method of claim 1 further comprising amplifying the at least one plurality of oligonucleotides to produce a plurality of amplified oligonucleotides.

3. The method of claim 2 further comprising exposing the plurality of amplified oligonucleotides to a restriction enzyme under conditions suitable to promote digestion.

4. The method of claim 2 further comprising subjecting the plurality of amplified oligonucleotides to error removal prior to or after exposing the plurality of amplified oligonucleotides to a restriction enzyme under conditions suitable to promote digestion.

5. The method of claim 4 wherein the plurality of amplified oligonucleotides are contacted with a mismatch binding agent, wherein the mismatch binding agent selectively binds and cleaves double-stranded oligonucleotides comprising a mismatch.

6. The method of claim 3 wherein the restriction enzyme is a type IIS restriction endonuclease.

7. The method of claim 1 wherein the padding nucleotide sequence is positioned between the primer recognition site and the restriction enzyme recognition site within the 5' flanking sequence.

8. The method of claim 1 wherein the padding nucleotide sequence is positioned upstream of the primer recognition site within the 5' flanking sequence.

9. The method of claim 1, wherein the padding nucleotide sequence is from 4 bps long to 10 bps long.

10. The method of claim 1 wherein the plurality of oligonucleotides comprise error containing oligonucleotides and error-free oligonucleotides.

11. The method of claim 1 wherein the method further comprises sequencing the oligonucleotides isolated from step c.

12. A redundant array comprising at least one plurality of oligonucleotide sequences, each oligonucleotide of each plurality of oligonucleotides having a different length and each oligonucleotide of each plurality of oligonucleotides having an identical predefined internal sequence, a 3' flanking sequence at the 3' end of the internal sequence and a 5' flanking sequence at the 5' end of the internal sequence, wherein the 3' flanking sequence comprises from 5' to 3', a restriction enzyme recognition site and a primer recognition site;

wherein the 5' flanking sequence comprises from 5' to 3', a primer recognition site and a restriction enzyme recognition site, and further comprises a padding nucleotide sequence, wherein each padding nucleotide sequence has a different length; and wherein the redundant array comprises redundant internal sequences.

13. The redundant array of claim 12 wherein the padding nucleotide sequence is positioned between the primer recognition site and the restriction enzyme recognition site within the 5' flanking sequence.

14. The redundant array of claim 12 wherein the padding nucleotide sequence is positioned upstream of the primer recognition site sequence is positioned upstream of the primer recognition site within the 5' flanking sequence.

15. The redundant array of claim 12 wherein each internal sequence is represented by two sets of oligonucleotides, a second set of oligonucleotides being a reverse-complement of a first set of oligonucleotides.

16. A composition for the assembly of a target nucleic acid having a predefined sequence comprising:

a. a first plurality of oligonucleotides comprising a first internal sequence identical to the 5' end of the target nucleic acid;

b. a second plurality of oligonucleotides comprising a second internal sequence identical to the 3' end of the target nucleic acid; and c. optionally one or more pluralities of oligonucleotides each comprising an internal sequence identical to a different portion of the sequence of the target nucleic acid, wherein each oligonucleotide of each plurality of oligonucleotides has a sequence region overlapping with a sequence region in each oligonucleotide of another plurality of oligonucleotides, wherein each internal sequence of the one or more pluralities of oligonucleotides together with the first and second internal sequences comprise the target nucleic acid;

wherein each oligonucleotide has 5' and 3' flanking sequences at the 5' end and the 3' end of each internal sequence, each of the flanking sequences comprising a primer recognition site and a restriction enzyme recognition site; and wherein each 5' flanking sequence further comprises a padding nucleotide sequence that has a different length than other padding sequences within each plurality of oligonucleotides.

17. The composition of claim 16 wherein the padding nucleotide sequence is positioned between the primer recognition site and the restriction enzyme recognition site within the 5' flanking sequence.

18. The composition of claim 16 wherein the padding nucleotide sequence is positioned upstream of the primer recognition site within the 5' flanking sequence.

19. The composition of claim 16 wherein the padding nucleotide sequence is from 4 bps long to 10 bps long.

20. The composition of claim 16 wherein the restriction enzyme recognition site is a type IIS restriction enzyme recognition site.

21. The composition of claim 16, wherein the one or more pluralities of oligonucleotides of part c are present in the composition.

* * * * *